(12) United States Patent
Dunn et al.

(10) Patent No.: US 9,845,569 B2
(45) Date of Patent: Dec. 19, 2017

(54) FLAME RESISTANT FABRIC HAVING ANTIMICROBIALS AND METHODS FOR MAKING THEM

(75) Inventors: Charles S. Dunn, Mableton, GA (US); Michael T. Stanhope, Atlanta, GA (US); Michael A. Laton, Fayetteville, GA (US); Rembert J. Truesdale, III, Thomaston, GA (US)

(73) Assignee: Southern Mills, Inc., Union City, GA (US)

( * ) Notice: Subject to any disclaimer, the term of this patent is extended or adjusted under 35 U.S.C. 154(b) by 1990 days.

(21) Appl. No.: 11/637,648

(22) Filed: Dec. 12, 2006

(65) Prior Publication Data
US 2011/0023206 A1 Feb. 3, 2011

Related U.S. Application Data

(60) Provisional application No. 60/749,909, filed on Dec. 12, 2005, provisional application No. 60/750,685, filed on Dec. 14, 2005.

(51) Int. Cl.
*D06M 16/00* (2006.01)
*D06M 13/07* (2006.01)
(Continued)

(52) U.S. Cl.
CPC .......... *D06M 16/00* (2013.01); *A41D 31/0022* (2013.01); *A41D 31/0077* (2013.01);
(Continued)

(58) Field of Classification Search
CPC ............ A41D 31/0022; A41D 31/0077; A61L 2300/404; A61L 31/16; A62B 17/003; D06M 13/07; D06M 6/00; D06M 2200/30
(Continued)

(56) References Cited

U.S. PATENT DOCUMENTS

| 3,884,626 A | 5/1975 | Hoster et al. |
|---|---|---|
| 4,324,706 A | 4/1982 | Tabe et al. |
| (Continued) | | |

FOREIGN PATENT DOCUMENTS

| AU | 2006350046 B2 | 12/2011 |
|---|---|---|
| FR | 2 836 932 A | 9/2003 |
| (Continued) | | |

OTHER PUBLICATIONS

Microsafe.TM Technical Bulletin, published by Celenese Acetate, copyright 1998.*

(Continued)

*Primary Examiner* — Jennifer A Steele
(74) *Attorney, Agent, or Firm* — Kilpatrick Townsend & Stockton LLP

(57) ABSTRACT

Flame resistant fabrics having antimicrobial properties that combat odor and/or resist hazardous microorganisms. The fabrics are particularly suitable for use in clothing and more particularly in protective garments designed to be worn by individuals, such as military personnel and emergency rescue personnel, at risk of exposure to fire and extreme temperatures as well as hazardous substances. The fabrics may be formed in a variety of ways, including, but not limited to, incorporating antimicrobial fibers into the flame resistant fabric yarn or by treating the pre-formed flame resistant yarn or fabric with antimicrobial agents in a dyeing or finishing process.

10 Claims, 1 Drawing Sheet

(51) Int. Cl.

| | |
|---|---|
| *D06M 15/643* | (2006.01) |
| *D06M 13/17* | (2006.01) |
| *D06M 13/156* | (2006.01) |
| *D06M 13/152* | (2006.01) |
| *D06M 13/08* | (2006.01) |
| *A41D 31/00* | (2006.01) |
| *D06M 11/83* | (2006.01) |
| *A61L 31/16* | (2006.01) |
| *A62B 17/00* | (2006.01) |

(52) U.S. Cl.
CPC .............. *A61L 31/16* (2013.01); *D06M 11/83* (2013.01); *D06M 13/07* (2013.01); *D06M 13/08* (2013.01); *D06M 13/152* (2013.01); *D06M 13/156* (2013.01); *D06M 13/17* (2013.01); *D06M 15/643* (2013.01); *A61L 2300/404* (2013.01); *A62B 17/003* (2013.01); *D06M 2200/30* (2013.01); *Y10T 442/2525* (2015.04)

(58) Field of Classification Search
USPC ......... 442/123, 136–147, 301, 327; 428/920, 428/921
See application file for complete search history.

(56) References Cited

U.S. PATENT DOCUMENTS

| | | | |
|---|---|---|---|
| 4,803,256 A | 2/1989 | Luckenbach | |
| 4,837,079 A | 6/1989 | Quantrille et al. | |
| 4,994,317 A | 2/1991 | Dugan et al. | |
| 5,024,851 A | 6/1991 | Goad et al. | |
| 5,221,287 A | 6/1993 | Reinert | |
| 5,269,840 A | 12/1993 | Morris et al. | |
| 5,527,597 A * | 6/1996 | Stanhope et al. | 442/184 |
| 5,650,213 A | 7/1997 | Rizika et al. | |
| 5,700,742 A * | 12/1997 | Payne | 442/123 |
| 5,856,005 A * | 1/1999 | Gurian | 428/370 |
| 5,900,978 A | 5/1999 | Sagar et al. | |
| 6,200,355 B1 | 3/2001 | Gadoury | |
| 6,679,922 B1 | 1/2004 | Sun et al. | |
| 6,759,127 B1 | 7/2004 | Smith et al. | |
| 6,858,550 B2 * | 2/2005 | Ahluwalia | 442/136 |
| 2003/0056297 A1 * | 3/2003 | Sun | 8/115.51 |
| 2003/0168401 A1 * | 9/2003 | Koslow | 210/500.25 |
| 2004/0198125 A1 * | 10/2004 | Mater et al. | 442/394 |
| 2005/0106967 A1 | 5/2005 | Suzuki | |
| 2005/0182140 A1 * | 8/2005 | Payne | 514/643 |
| 2007/0044801 A1 * | 3/2007 | Mathis et al. | 128/206.19 |
| 2007/0048344 A1 * | 3/2007 | Yahiaoui et al. | 424/405 |
| 2007/0169278 A1 | 7/2007 | Shigita et al. | |

FOREIGN PATENT DOCUMENTS

| | | |
|---|---|---|
| JP | 05-033270 A | 2/1993 |
| JP | H05-033270 A | 2/1993 |
| JP | H09-504343 | 4/1997 |
| JP | 11-000250 | 1/1999 |
| JP | 11-189978 A | 7/1999 |
| JP | 2004-115970 | 4/2004 |
| JP | 2004-143607 A | 5/2004 |
| JP | 5422206 | 11/2013 |
| WO | 9512021 A1 | 5/1995 |
| WO | 2005/012630 A | 2/2005 |

OTHER PUBLICATIONS

MicroChek.TM, p. 269, Handbook of Preservatives, copyright 2004, 2009, published by Synapse Information Resources.*
Definition of Woven, Textile Glossary, copyright 2001, Celanese Actetate.*
Finish, Finishing, Textile Glossary, copyright 2000, Celanese Acetate.*
Gao and Cranston "Recent Advances in Antimicrobial Treatments of Textiles"; Textile Research Journal; vol. 78(1): 60-72 DOI; www.trj.sagepub.com copyright 2008 SAGE publications.*
International Search Report and Written Opinion, PCT/US2007/046997, dated Sep. 5, 2008.
Office Action, Japanese Patent Application No. 2008-545691, dated Dec. 20, 2011.
Response to Office Action, European Patent Application No. 06851785.3, filed Nov. 15, 2012.
Office Action, Canadian Patent Application No. 2,632,938, dated Aug. 8, 2012.
Response to Office Action, Canadian Patent Application No. 2,632,938, filed Feb. 6, 2013.
Office Action, Canadian Patent Application No. 2,632,938, dated May 15, 2013.
Response to Office Action, Japanese Patent Application No. 2008-545691, filed Jun. 5, 2012.
Office Action, Japanese Patent Application No. 2008-545691, dated Apr. 2, 2013.
Office Action, Canadian Application No. 2,632,938, dated Feb. 5, 2014.
Office Action, Japanese Patent Application No. 2013-206496, dated Nov. 4, 2014.
Office Action, Japanese Patent Application No. 2013-206496, dated Sep. 15, 2015.
Office Action, European Patent Application No. 06851785.3, dated Oct. 12, 2015.
Office Action, European Patent Application No. 06851785.3, dated May 8, 2012.

* cited by examiner

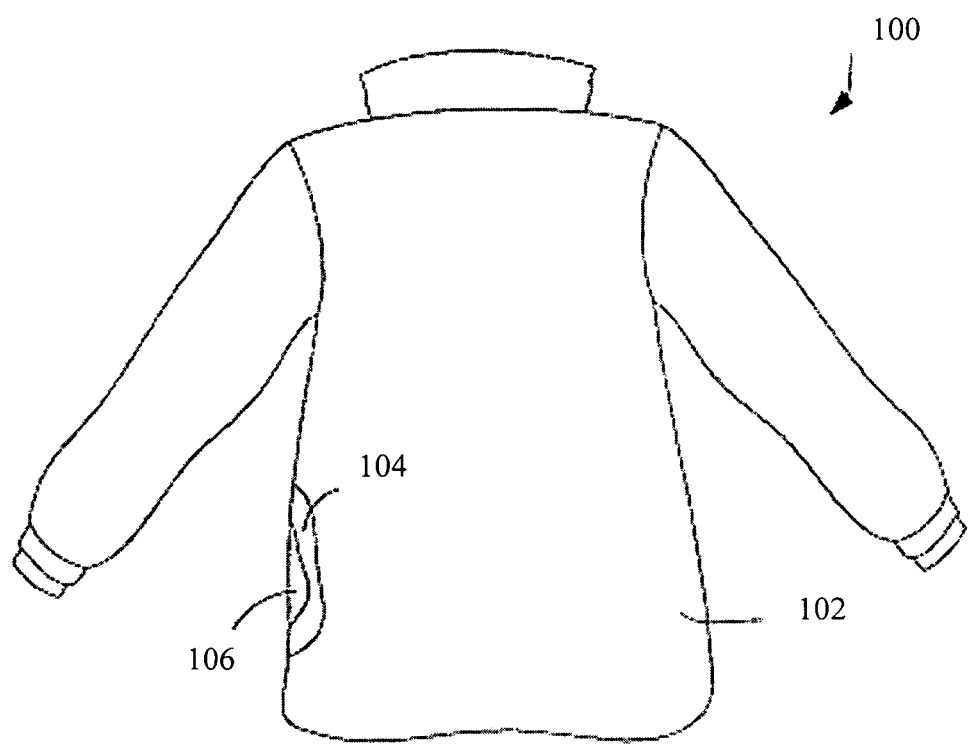

FLAME RESISTANT FABRIC HAVING ANTIMICROBIALS AND METHODS FOR MAKING THEM

RELATED APPLICATION DATA

This is a utility patent application, which claims the benefit of U.S. Provisional Application No. 60/749,909, filed Dec. 12, 2005, and U.S. Provisional Application No. 60/750,685, filed Dec. 14, 2005, both of which are incorporated herein by reference in their entirety.

FIELD OF THE INVENTION

This invention relates to flame resistant fabrics having antimicrobials.

BACKGROUND OF THE INVENTION

Military personnel, such as aviators and ground personnel, and emergency personnel, such as firefighters and other first responders arriving at an emergency scene, risk exposure to a variety of hazardous environments including fire and/or extreme temperatures. As a result, they have traditionally been provided with protective clothing having flame resistant properties (e.g., self-extinguishing) to protect the wearer against extreme heat and fire. Such personnel must oftentimes wear their protective clothing for extended periods of time while subjected to these extreme conditions. Not surprisingly, the clothing eventually begins to smell. Heretofore, these special flame resistant clothes have been devoid of any means by which to combat or control odor.

Moreover, different clothing has been provided to protect military and emergency personnel in different hazardous environments. As explained above, flame resistant clothing is provided in the event of fire or extreme temperatures. However, separate hazardous material suits must be donned if the emergency involves hazardous substances such as chemical, radiological, or biological agents.

The NFPA (National Fire Protection Association) has incorporated chemical, biological, and nuclear protection standards in an upcoming revision to the NFPA 1971 Standard for Structural Firefighting. To meet this standard, garments for firefighters may need to incorporate chemical, biological, and nuclear particulate protection—protections which traditional flame resistant firefighter clothing (called turnout gear) have not afforded.

Thus, there exists a need to provide flame resistant fabric capable of controlling odor and/or resisting hazardous microorganisms.

SUMMARY OF THE INVENTION

This invention provides flame resistant fabrics having antimicrobials that combat odor and/or resist hazardous microorganisms. The fabric is particularly suitable for use in clothing and more particularly in protective garments designed to be worn by individuals, such as military personnel and emergency rescue personnel, at risk of exposure to fire and extreme temperatures as well as hazardous substances.

The flame resistant, antimicrobial fabrics of this invention may be formed in a variety of ways. In one embodiment, antimicrobial fibers are formed into yarn that is subsequently woven or knitted into a fabric. Pre-formed polymer fibers may be coated with antimicrobial additives to create antimicrobial fibers. Alternatively, antimicrobial additives may be added during the fiber forming process so that the antimicrobial additives are at least partially embedded in the final antimicrobial fibers. The resulting antimicrobial fibers may then be formed into yarn. The antimicrobial fibers can be mixed with flame resistant fibers and the fiber mixture formed into flame resistant, antimicrobial yarns that are subsequently woven or knitted to form the desired flame resistant, antimicrobial fabric.

In an alternative embodiment, the antimicrobial fibers are not incorporated directly into the yarn which is subsequently formed into the fabric. Rather, antimicrobial agents are applied, such as in a dyeing process or a finishing process, to pre-formed yarn or pre-formed fabric to impart the desired antimicrobial properties.

The fabrics of this invention are not limited to woven or knitted fabrics. Rather, antimicrobial fibers may be incorporated into a nonwoven flame resistant fabrics, such as, for example, via needlepunching.

It thus is an object of this invention to provide a flame resistant, antimicrobial fabric.

It is another object of this invention to provide a flame resistant, antimicrobial fabric for a protective garment.

It is yet another object of this invention to provide methods for making flame resistant, antimicrobial fabrics.

It is still another object of this invention to provide methods for making a flame resistant, antimicrobial fabric for a protective garment.

Other objects, features, and advantages of the present invention will be apparent to those skilled in the art with reference to the remaining text and drawings of this application.

BRIEF DESCRIPTION OF THE DRAWINGS

FIG. 1 is a partially cut away view of a protective garment that includes a flame resistant, antimicrobial fabric in accordance with an embodiment of the present invention.

DETAILED DESCRIPTION

This invention relates to flame resistant fabrics having antimicrobial properties. The fabrics disclosed herein are particularly well-suited for use in clothing, and more particularly in clothing, such as emergency response garments and military uniforms, in which the wearer may be subjected to extreme temperatures and/or hazardous substances.

FIG. 1 illustrates an example of a protective garment 100 for which the fabric of this invention is particularly well-suited. The garment 100 can be a firefighter turnout coat (shown in FIG. 1) or any other garment or garment layers for which the wearer can benefit from the flame resistant and anti-bacterial properties of the fabrics described herein, including, but not limited to, shirts, pants, jackets, coveralls, vests, t-shirts, underwear, gloves, hats and helmets, liners for gloves, hats, helmets, boots, etc. and the like. The present invention is not limited to garments, but can include other uses for flame resistant, antimicrobial fabrics irrespective of their application.

The garment 100 shown in FIG. 1 includes an outer shell 102 that forms an exterior surface of the garment 100, a barrier layer 104 that forms an intermediate layer of the garment, and a thermal liner 106 that forms an interior surface of the garment 100. For general reference, the exterior surface or outer shell 102 can be directly exposed to the environment the user or wearer is operating in, and the interior surface or thermal liner 106 is a surface that contacts the user or wearer, or contacts the clothes the user or wearer may be wearing. In accordance with an embodiment of the invention, some or all of the layers 102, 104, 106 forming garment 100 can include the flame resistant, antimicrobial fabrics of this invention.

The flame resistant, antimicrobial fabrics of this invention may be formed in a variety of ways. In one embodiment, antimicrobial fibers are formed into yarn that is subsequently woven or knitted into a fabric. While inherently antimicrobial fibers such as bamboo and hemp may be used, antimicrobial additives may be added to polymer fibers (such as, for example, nylon, polyester, acrylic, polyolefin, polypropylene, polyethylene, polyurethane, etc.) to form the antimicrobial fibers. Suitable antimicrobial additives, include, but are not limited to, silver, copper, and triclosan.

Pre-formed polymer fibers may be coated (either partially or entirely) with antimicrobial additives to create antimicrobial fibers ("coated antimicrobial fibers"). Alternatively, antimicrobial additives may be added during the fiber forming process (e.g., an extrusion process) so that the antimicrobial additives are at least partially embedded in the final antimicrobial fibers ("embedded antimicrobial fibers").

Suitable antimicrobial fibers are commercially available and include, but are not limited to, X-STATIC® (distributed by Noble Fiber Technologies, Inc. of Clarks Summit, Pa. (www.x-static.com)); E47® (distributed by A.R.C. Technologies (www.e47nano.com)); Cupron® fibers (www.cupron.com); MIPAN® Nano Magic Silver® (distributed by Hyosung (http://www.mipan.co.kr/eng/products/magic silver.html)); Fossshield® (distributed by Foss Manufacturing Co., LLC ((http://www.fossmfg.com/bu_fosshield.cfm)); Shieldex® (distributed by Statex® Production and Manufacturing Company, Swico Fil Ag Textile Services ((http://www.swicofil.com/statexshieldex.html)).

The resulting antimicrobial fibers are then formed into yarn. In one embodiment, the antimicrobial fibers (either alone or mixed with non-flame resistant, non-antimicrobial fibers) may be formed into antimicrobial yarn, which is then woven with flame resistant yarn (such as that made with flame resistant fibers) to form a flame resistant, antimicrobial fabric. In an alternative and preferable embodiment, the antimicrobial fibers are mixed with flame resistant fibers and the fiber mixture is formed into flame resistant, antimicrobial yarn. This yarn is then woven or knitted to form the desired flame resistant, antimicrobial fabric. One embodiment of the fabric of this invention has a weight within the range of 2-20 ounces per square yard and more preferably 3-7.5 ounces per square yard, inclusive.

Suitable flame resistant fibers include, but are not limited to, para-aramid fibers, meta-aramid fibers, and other inherently flame resistant fibers including, but not limited to, FR rayon, polybenzoxazole (PBO), polybenzimidazole (PBI), melamine, polyamide, polyimide, polyimideamide, modacrylic, and polypyridobisimidazole (PIPD).

Examples of suitable para-aramid fibers include, but are not limited to, fibers available under the trademarks KEVLAR® (DuPont), TECHNORA®, and TWARON® (Teijin). Examples of suitable meta-aramid fibers include, but are not limited to, fibers available under the tradenames NOMEX T-450® (100% meta-aramid), NOMEX-455® (a blend of 95% NOMEX® and 5% KEVLAR®), and NOMEX T-4620 (a blend of 93% NOMEX®, 5% KEVLAR®, and 2% anti-static carbon/nylon), each of which is produced by DuPont Corporation. Examples of meta-aramid fibers can also include fibers available under the trademark CONEX®, which are produced by the Teijin Group. An example of a PBO fiber is ZYLON® from Toyobo®. One example of a suitable polypyridobisimidazole (PIPD) fiber is M5®, available from Magellan Systems International.

In addition or in the alternative to using inherently flame resistant fibers, non-inherently flame resistant fibers, such as, but not limited to, cellulosic fibers like rayon, cotton, acetate, triacetate, and lyocell, can be rendered flame resistant by treating such fibers with a suitable flame retardant. Therefore, flame resistant fibers that are not inherently flame resistant can be, but do not have to be, used to make the fabrics of this invention.

Any ratio of antimicrobial fibers to flame resistant fibers may be used to form the flame resistant, antimicrobial fabric. However, it is preferable, but certainly not necessary, that the antimicrobial fibers comprise 3-30% by weight of the finished fabric. In one embodiment, coated antimicrobial fibers comprise 5-10% by weight of the finished fabric. In an alternative embodiment, embedded antimicrobial fibers comprise approximately 20% by weight of the finished fabric. It should be noted however that some antimicrobial fibers have a tendency to burn. Thus, if the fabric comprises more than 10% by weight of antimicrobial fibers, it may be desirable, but not mandatory, to treat the fabric with additional flame resistant agents (or include additional flame resistant fibers such as modacrylic in the yarns).

In an alternative embodiment, the antimicrobial fibers are not incorporated directly into the yarn which is subsequently formed into the fabric. Rather, antimicrobial agents can be applied to pre-formed yarn or pre-formed fabric to impart the desired antimicrobial properties. In one such embodiment, antimicrobial agents may be added during the yarn or fabric dying process, wherein the amount of active agent exhausted into the fabric is preferably, but not necessarily, between 0.1% to 30%, inclusive, by weight of the fabric.

In another embodiment, antimicrobial agents may be applied to the fabric in a finishing process. In one such process, but certainly not the only available process, an antimicrobial agent, suitable binders (e.g., acrylic polymers and co-polymers, polyurethanes, SBR (styrene butadiene resin), melamine, or polyvinylidene chlorides or combinations thereof), and other traditional additives (i.e. FR additives, softeners, durable press resins, wetting agents, wicking agents, etc.) are applied to the fabric using known finishing or coating application equipment such as padding, spraying, foam application, knife over roll, gravure roll, kiss roll, etc. After such application, the resulting fabric is dried and cured under proper conditions (e.g., 212° F.-430° F. for 5 seconds to 4 minutes) to fix the antimicrobial agent to the fabric. The amount of active antimicrobial agent fixed to the fabric is preferably, but not necessarily, between 0.1% to 30%, inclusive, by weight of the fabric.

While in these embodiments, the antimicrobial agents may be added to flame resistant yarns and fabrics, note that the flame resistant properties (in addition to the antimicrobial properties) may be imparted in a dyeing or finishing process as well.

Antimicrobial agents suitable for use in a dyeing and/or a finishing process include, but are not limited to: (1) triclosan (a diphenyl ether derivative available from Huntsman Corporation in Salt Lake City, Utah as TINOSAN® AM110); (2) silver (including silver with a polymer binder (e.g., Ultra-Fresh Silpure FBR-5 Mixed available from Thomson Research Associates) or nano-silver (e.g., SMARTSILVER® available from NanoHorizons in State College, Pa.)); (3) PHMB (polyhexamethylene biguanide hydrochloride, sold by Arch Biocides Limited under the trademark Reputex®); (4) quaternary silicone (such as AEM 5700 from Aegis Environments); (5)N-Halamine (such as Haloshield® available from Halosource Corporation of Redmond, Wash.); and (6) cross-linked polyethylene glycols (e.g., PEG Glycol, 2-methyl-1,3 propane diol, propylene glycol, dipropylene glycol, tripropylene glycol, 1,3 butylene glycol).

While the flame resistant, antimicrobial fabrics of this invention have thus far been described as woven or knitted fabrics, by no means is the invention limited to such fabrics. Rather, the antimicrobial fibers may be incorporated into nonwoven flame resistant fabrics, such as, for example, via needlepunching.

The fabrics of this invention preferably perform at the level recommended by the applicable standards and testing methodologies. For example, the fabrics preferably exhibit flame resistant properties in accordance with applicable military standards (e.g., MIL-C-83429B) and firefighting standards (e.g., at least NFPA 2112, 1971, 1951, and 1977) when tested in accordance with ASTM D6413. The fabrics preferably have a char length of less than or equal to six inches and more preferably less than or equal to four inches. ASTM E2180 and AATCC TM100 and TM147 may be used to measure the antimicrobial properties of the fabrics of this invention.

The foregoing is provided for purposes of illustrating, explaining, and describing exemplary embodiments and certain benefits of the present invention. Modifications and adaptations to the illustrated and described embodiments will be apparent to those skilled in the art and may be made without departing from the scope or spirit of the invention.

We claim:

1. A flame resistant fabric comprising modacrylic fibers and an active antimicrobial additive dyed or finished into the flame resistant fabric such that the additive is uniformly dispersed throughout the fabric, wherein the active antimicrobial additive comprises polyhexamethylene biguanide hydrochloride.

2. The fabric of claim 1, wherein the fabric further comprises an additional antimicrobial additive.

3. The fabric of claim 2, wherein the additional antimicrobial additive is selected from the group consisting of silver, copper, triclosan, a silane quaternary ammonium compound, N-Halamine, and cross-linked polyethylene glycol.

4. The fabric of claim 2, wherein the additional antimicrobial additive is applied to the fabric as a coating.

5. The fabric of claim 1, wherein the fabric is woven or knitted.

6. The fabric of claim 1, wherein the fabric is a nonwoven.

7. A garment comprising the fabric of claim 1.

8. The fabric of claim 2, wherein the additional antimicrobial additive comprises antimicrobial fibers.

9. The fabric of claim 1, wherein the fabric further comprises cellulosic fibers.

10. The fabric of claim 1, wherein the active antimicrobial additive comprises between 0.1% to 30% by weight of the fabric.

* * * * *